Figure 2:
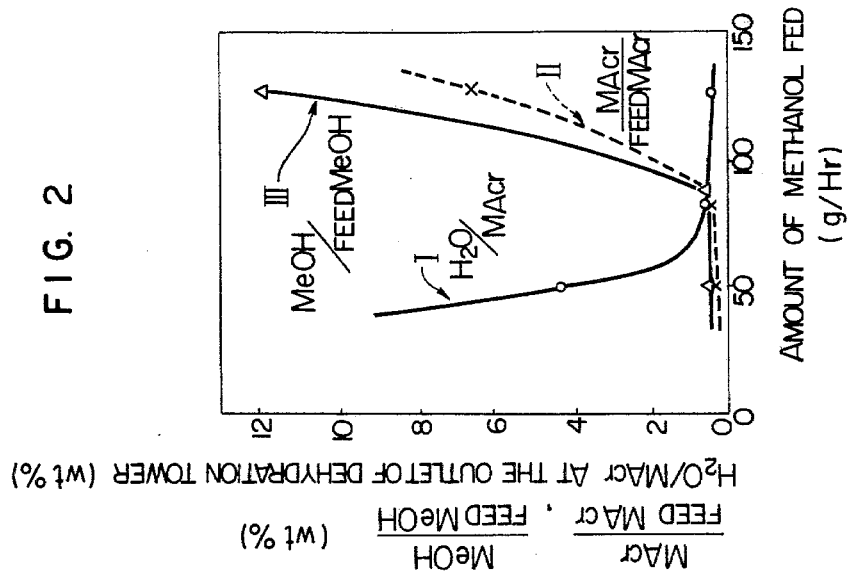

United States Patent [19]

Aoshima et al.

[11] 4,329,513

[45] May 11, 1982

[54] METHOD FOR DEHYDRATION OF UNSATURATED ALDEHYDE-CONTAINING GAS

[75] Inventors: Atsushi Aoshima, Yokohama; Ryoichi Mitsui; Toshiaki Kaneko, both of Fuji, all of Japan

[73] Assignee: Asahi Kasei Kogyl Kabushiki Kaisha, Osaka, Japan

[21] Appl. No.: 213,703

[22] Filed: Dec. 5, 1980

[30] Foreign Application Priority Data

Dec. 19, 1979 [JP] Japan .................. 54/164098

[51] Int. Cl.³ .................. C07C 45/58; C07C 47/20
[52] U.S. Cl. .................. 568/492; 562/449
[58] Field of Search .................. 568/492, 449

[56] References Cited

U.S. PATENT DOCUMENTS

| | | | |
|---|---|---|---|
| 2,514,966 | 7/1950 | Pierotti et al. | 568/492 |
| 2,514,967 | 7/1950 | Pierotti et al. | 568/492 |
| 2,767,216 | 10/1956 | Evans et al. | 568/492 |
| 3,828,099 | 8/1974 | Sato et al. | 568/492 |
| 3,957,880 | 5/1976 | Sato et al. | 568/492 |

Primary Examiner—Werren B. Lone
Attorney, Agent, or Firm—Sprung, Horn, Kramer & Woods

[57] ABSTRACT

Methanol is allowed to flow downwardly and contacted countercurrently with an unsaturated aldehyde-containing gas obtained from gas phase catalytic oxidation of the starting gas containing at least one gas selected from the group consisting of propylene, isobutylene and t-butanol, said methanol being supplied in such an amount that substantially the whole thereof can be gasified in the treatment. According to this method, the water content in said unsaturated aldehyde-containing gas can be rendered smaller than that in the azeotropic mixture of the unsaturated aldehyde and water, and also there takes place no polymerization of the unsaturated aldehyde.

5 Claims, 2 Drawing Figures

METHOD FOR DEHYDRATION OF UNSATURATED ALDEHYDE-CONTAINING GAS

This invention relates to a method for removing water contained in a gas which contains an unsaturated aldehyde (acrolein or methacrolein) and which is derived from gas phase catalytic oxidation of propylene, isobutylene, t-butanol or a mixture thereof. More particularly, this invention relates to a method for removing water contained in said gas without any loss of the unsaturated aldehyde due to polymerization to render the water content in said gas smaller than that in the azeotropic mixture of the unsaturated aldehyde and water.

Recently, studies have been made actively on methods for producing an unsaturated aldehyde, that is, acrolein or methacrolein, by mixing propylene, isobutylene, t-butanol or a mixture thereof with an oxygen-containing gas and subjecting the resulting mixture to catalytic oxidation in the presence of a catalyst at a high temperature (300°–500° C.).

Acrolein or methacrolein is used as a material for the preparation of useful compounds such as acrylic acid or methacrylic acid, but for certain uses of such compounds, it is required that the water content of the material is as small as possible. Such requirement is keen when, for instance, producing methyl methacrylate (or methyl acrylate) directly from methacrolein (or acrolein), methanol and oxygen. In such a case, it is desired that the water content based on the unsaturated aldehyde is smaller than the water content in the azeotropic mixture of the unsaturated aldehyde and water (in the case of methacrolein, 7.7% by weight based on methacrolein, and in the case of acrolein, 2.6% by weight based on acrolein), particularly not more than 2% by weight.

However, the water content of the unsaturated aldehyde-containing gas obtained from said gas phase catalytic oxidation exceeds said value because such a gas contains water vapor produced from the reaction and/or water vapor used as a reaction diluent, in addition to the unsaturated aldehyde and by-products.

As a method of treating said unsaturated aldehyde-containing gas, there is known as method by which the unsaturated aldehyde is extracted from the reaction product gas with an alcohol and the extract is then distilled (for example, see Japanese patent application Kokai (Laid-Open) No. 92,007/74), but according to this method, since the water existing in the reaction product gas is also absorbed into said alcohol, only an azeotropic mixture of the unsaturated aldehyde and water is obtained even if the extract is distilled, and it is impossible to render the water content in the unsaturated aldehyde smaller than that in the azeotropic mixture.

There is also known a method by which the reaction product gas is absorbed in water (U.S. Pat. No. 2,514,966), but this method is less capable of rendering the water content in the unsaturated aldehyde below that in the azeotropic mixture for the same reason.

As a method for removing water even more perfectly from the unsaturated aldehyde-containing gas, there is known a technique according to which the gas is first extracted with a solvent such as a hydrocarbon and the extract is then distilled, but this method involves many problems in its practical application because said method is complicated in operation and also the unsaturated aldehyde is apt to polymerize during the distillation operation since the substantially pure, low-water-content unsaturated aldehyde is heated.

Treatment of the unsaturated aldehyde-containing gas with a generally known desiccant is of little practical value because such a desiccant has a poor dehydrating ability and there is rather caused a great loss of the unsaturated aldehyde due to polymerization on the desiccant surface.

The present inventors have conducted further research on a method for very simply obtaining a dehydrated unsaturated aldehyde without causing any loss of the unsaturated aldehyde due to polymerization and have found as a result that the object can be attained by condensing and separating water in the unsaturated aldehyde-containing gas by utilizing the heat of gasification of methanol.

An object of this invention is, therefore, to provide a method for producing an unsaturated aldehyde having a smaller water content than that in the azeotropic mixture of the unsaturated aldehyde and water.

Another object of this invention is to provide a method for easily producing an unsaturated aldehyde with a small water content without causing any loss of the unsaturated aldehyde due to polymerization.

According to the present invention, there is provided a method for dehydrating an unsaturated aldehyde-containing gas, which comprises allowing methanol to flow downwardly and contacting the same countercurrently with an unsaturated aldehyde-containing gas obtained from gas phase catalytic oxidation of the starting material containing at least one substance selected from the group consisting of propylene, isobutylene and t-butanol, and methanol being supplied in such an amount that substantially the whole of the methanol supplied can be gasified in the treatment.

The gist of this invention lies in that methanol is allowed to flow downwardly and contacted countercurrently with an unsaturated aldehyde-containing gas produced from the gas phase catalytic oxidation, whereby the heat of gasification for methanol is taken from the unsaturated aldehyde-containing gas in contact with the methanol when methanol is gasified, and the water in the gas is condensed and separated. Since the unsaturated aldehyde is dehydrated while being maintained in the gas phase, substantially no loss is caused by polymerization. Therefore, said dehydration method is practicable.

The unsaturated aldehyde-containing gas obtained from the gas phase catalytic oxidation may be immediately subjected to countercurrent contact with methanol, but it is preferable to perform said countercurrent contact after the unsaturated aldehyde-containing gas has been cooled by a suitable commonly employed method to decrease the contents of the acids, high-boiling substances and water vapor produced by the reaction as well as the water vapor used as reaction diluent.

Figure 1:
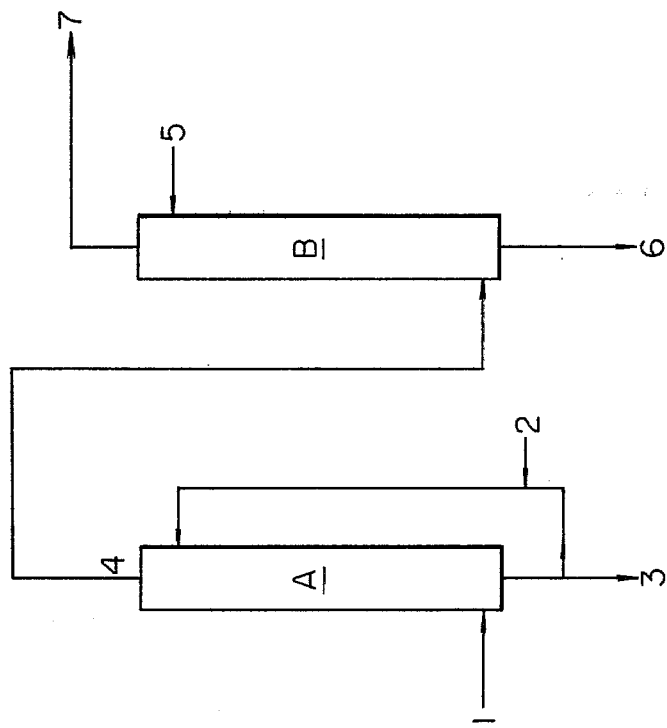

This invention is illustrated below referring to the accompanying drawings, in which FIG. 1 is a flow sheet showing an embodiment of this invention, and FIG. 2 is a graph showing changes of various data with a variation of the amount of methanol fed.

In FIG. 1, a reaction product gas 1 produced in a gas phase catalytic oxidation reactor is introduced into a quenching tower A at the bottom and contacted with water 2 supplied into said quenching tower A at the top, thereby cooling said gas 1. The water condensed by cooling is recycled after the cooling step while a part thereof is discharged as waste water 3. A polymerization inhibitor such as hydroquinone is added to water 2.

By this cooling step, the reaction product gas 1 can be quickly cooled to a temperature of from room temperature to 95° C., preferably from 30° to 80° C.

Also, by this cooling step, the water-soluble gases such as methacrylic acid, acrylic acid, acetic acid, etc., contained in the reaction product gas 1 as by-products can be taken out of the reaction product gas 1 together with water 2. The high-boiling by-products can also be liquefied and removed.

On the other hand, the unsaturated aldehyde-containing gas taken from the top of the quenching tower A is introduced into a dehydration tower B at the bottom and methanol is supplied into the dehydration tower B at the top, when the methanol is contacted countercurrently with said unsaturated aldehyde-containing gas 4, whereby substantially the whole amount of the methanol supplied is gasified. At this time, the unsaturated aldehyde-containing gas 4 is deprived of an amount of heat corresponding to the heat of gasification of methanol 5, whereby the water vapor contained in the gas condenses and falls down to the bottom of the dehydration tower B, from which it is discharged as liquid 6. The thus dehydrated unsaturated aldehyde-containing gas 4 is taken out from the top of the dehydration tower B along with the gasified methanol 5 as shown by 7 in FIG. 1.

The thus obtained dehydrated unsaturated aldehyde-containing gas 7 is far smaller in water content than the azeotropic composition of the unsaturated aldehyde and water.

The liquid 6 discharged from the bottom of the dehydration tower B may be either released out of the system and discarded or may be recycled for reuse as cooling water 2.

In the system shown in FIG. 1, the quenching tower A may be joined to a lower part of the dehydration tower B to form an integral tower unit.

The methanol 5 used in the dehydration step is preferably substantially free of water, and pure methanol is most preferable. However, it may contain small quantities of substances which do not adversely affect the operation in the dehydration step.

In the dehydration step, the amount of methanol fed is a very important factor; it is essential that the amount of methanol supplied is such that substantially the whole amount thereof is gasified by the unsaturated aldehyde-containing gas supplied. Feed of an excess of methanol 5 causes the unsaturated aldehyde to dissolve in the excess methanol 5 and the unsaturated aldehyde is allowed to be effluent from the bottom of the dehydration tower B.

The amount of methanol 5 supplied is difficult to define uniquely because the amount varies depending on the inlet temperature of the dehydration tower B, the water content in the unsaturated aldehyde-containing gas and the amount of the gas to be treated, but usually methanol is supplied in an amount of 10 to 1,000 g, preferably 30 to 400 g, per 1 m$^3$ of the unsaturated aldehyde-containing gas. By supplying a proper amount of methanol 5, the H$_2$O/methacrolein ratio, for instance, can be reduced to a range 1/100 to 1/1,000.

The operating pressure in the dehydration step may be such as to be decided by feed of the unsaturated aldehyde-containing gas, but usually it is close to normal pressure. The operating temperature is usually within the range of from 0° to 90° C. The lower the temperature, the smaller the amount of methanol gasified, but since the amount of saturated water vapor is also accordingly reduced, the process of this invention will not become impossible to carry out even at low temperatures.

In order to stabilize the unsaturated aldehyde in the dehydration tower, it is desirable to allow a polymerization inhibitor to be present therein, and hence, it is preferable to allow an appropriate amount of a polymerization inhibitor to be present in methanol 5. As the polymerization inhibitor, any generally known one may be used, such as hydroquinone, 2,6-di-tertiary butyl-4-methylhydroquinone, phenothiazine or the like.

In another embodiment of this invention, methanol may be supplied into the dehydration tower B from a middle part thereof simultaneously with supplying methanol from the top of the tower B. In this case, the methanol supplied from the middle part may be hydrous.

Thus, according to the present invention, it is possible to obtain an unsaturated aldehyde-containing gas with a smaller water content than that in the azeotropic mixture of the unsaturated aldehyde and water by a simple process, and hence the thus obtained unsaturated aldehyde-containing gas can be favorably used as a starting material for the direct production of the unsaturated acid esters. For instance, the process of this invention can be combined by such a simple process for synthesizing methyl methacrylate (or methyl acrylate) that the dehydrated methacrolein- or (acrolein-)containing gas is fed as it is to an oxidation-esterification reactor, or alternatively, the dehydrated unsaturated aldehyde-containing gas can be introduced into an absorption tower to allow it to be absorbed in an absorbent, such as methanol, a hydrocarbon, methyl methacrylate or acrylate or the like to form, for example, a methacrolein (or acrolein) solution, which can be used as the starting material for the oxidation-esterification reaction. Thus, an integrated process for producing methyl ester of an unsaturated carboxylic acid can easily be established. When an absorption tower is used, there is produced an additional effect of elevating the absorption efficiency in the absorption tower because the gas temperature is lowered when methanol is gasified by the mixed gas as mentioned above and hence it follows that the dehydrated unsaturated aldehyde-containing gas at a low temperature enters the absorption tower.

When the unsaturated aldehyde is stored the presence of a polymerization inhibitor is desired, and hence, it is preferable to allow an appropriate amount of a polymerization inhibitor to be present in the absorbent. As the polymerization inhibitor, any generally known one may be used, such as hydroquinone, 2,6-di-tertiary butyl-4-methylhydroquinone, phenothiazine or the like.

Further, according to this invention, the unsaturated aldehyde-containing gas can be dehydrated while being maintained in the gas form, and therefore the loss of the unsaturated aldehyde by polymerization is minimized.

The invention is further explained below referring to Examples, which are merely by way of illustration and not by way of limitation.

EXAMPLE 1

A reaction product gas produced from gas phase catalytic reaction of isobutylene was supplied into a quenching tower to remove therefrom the high-boiling substances and acids by means of water to obtain a gas of the following composition: 4.3 mole % of methacrolein, 6.9 mole % of water, 88.7 mole % in total of nitrogen, oxygen, carbon dioxide and carbon monoxide gases and unreacted isobutylene, and 0.1 mole % of by-products such as acetone (the H₂O/methacrolein ratio was 39% by weight). The flow rate of said gas was 13 Nl./min. Said gas was fed into a packed column (packed with 3 mm $\phi$-diameter and 4 mm long Raschig rings) having a diameter of 40 mm $\phi$ and a length of 60 cm at the bottom, whereas methanol containing 0.01% by weight of hydroquinone was supplied into said packed column at the top at a rate of 88 g/hr. The gas temperature was 35° C. at the bottom of the tower and 15° C. at the top. The H₂O/methacrolein ratio (by weight) in the gas taken out of the tower top was 0.6%.

The gas taken out of the tower top was absorbed by methanol in a 30-step Oldershaw type absorption tower having a diameter of 32 mm $\phi$. The absorbing solution recovered from the bottom of the absorption tower had the following composition:

81.7% by weight of methanol, 18% by weight of methacrolein, 0.1% by weight of by-products, ketones such as acetone, and 0.13% by weight of water.

The amounts of methanol and methacrolein in the discharge liquid obtained from the bottom of the dehydration tower were 0.6% by weight of the amount of the methanol fed from the top of the dehydration tower and 0.5% by weight of the amount of the methacrolein recovered from the absorption tower, respectively.

EXAMPLE 2

A reaction product gas produced from a gas phase catalytic reaction of propylene was treated in a quenching tower with water to remove the high-boiling substances and acids, thereby obtaining a gas of the following composition: 4 mole % of acrolein, 6.9 mole % of water and 89.1 mole % in total of other substances including $N_2$, $O_2$, CO, $CO_2$, propylene and ketones ($H_2O$/acrolein=55.4% by weight). The gas flow rate was 13 Nl./min.

This gas was fed to the same packed column type dehydration tower as in Example 1 under the same conditions as in Example 1, except that 80 g of methanol was supplied into said tower at the top. The H₂O/acrolein ratio in the gas taken out of the tower top was 0.7% by weight.

EXAMPLE 3

A reaction product gas of the same composition (at the outlet of the quencing tower) as in Example 1 was treated in the same manner as in Example 1, except that the amount of methanol fed from the top of the dehydration tower was varied. The water to methacrolein ratio (H₂O/MAcr) at the tower top outlet, the ratio of methacrolein discharged from the tower bottom to methacrolein at the tower inlet (MAcr/Feed MAcr) and the ratio of methanol discharged from the tower bottom to methanol supplied to said tower MeOH/Feed MeOH) were measured, to obtain the results shown in the graph of FIG. 2. In the graph, curve I shows H₂O/MAcr, curve II shows MAcr/Feed MAcr and curve III shows MeOH/Feed MeOH.

EXAMPLE 4

A reaction product gas produced from a gas phase catalytic reaction of t-butanol was treated in a quenching tower with water to remove the high-boiling substances and acids, thereby obtaining a gas of the following composition: 4.6 mole % of methacrolein, 6.9 mole % of water and 88.5 mole % in total of other substances including nitrogen, oxygen, carbon dioxide, carbon monoxide, isobutylene and ketones. The gas flow rate was 13 Nl./min. (H₂O/methacrolein was 36.5% by weight).

This gas was fed to the same packed column type dehydration tower as in Example 1 under the same conditions as in Example 1, except that 80 g of methanol was supplied into said tower at the top. The H₂O/methacrolein ratio in the gas taken out of the tower was 0.56% by weight.

What is claimed is:

1. A method for dehydrating an unsaturated aldehyde-containing gas, which comprises allowing methanol to flow downwardly and contacting the same countercurrently at a temperature within the range of 0° C. to 90° C. and at a pressure close to normal with an unsaturated aldehyde-containing gas produced from gas phase catalytic oxidation of a starting gas comprising at least one gas selected from the group consisting of propylene, isobutylene and t-butanol, said methanol being supplied in such an amount from 10 g to 1 kg per 1 m³ of the unsaturated aldehyde-containing gas that substantially all the methanol can be gasified in the treatment.

2. A method for recovering an unsaturated aldehyde with a small water content, which comprises absorbing the gas dehydrated according to the method of claim 1 with methanol to recover the unsaturated aldehyde in the form of a methanol solution.

3. The method according to claim 1, wherein the amount of methanol fed is from 30 g to 400 g per 1 m³ of the unsaturated aldehyde-containing gas.

4. The method according to claim 1 or 3, wherein the methanol fed contains a polymerization inhibitor.

5. The method according to claim 4, wherein the polymerization inhibitor is hydroquinone.

* * * * *